US012635945B2

(12) United States Patent (10) Patent No.: US 12,635,945 B2
Xia et al. (45) Date of Patent: May 26, 2026

(54) SENSOR AND KNEE JOINT BRACE

(71) Applicants:VINCENT MEDICAL (DONG GUAN) MANUFACTURING CO., LTD, Guangdong (CN); VINCENT MEDICAL (DONG GUAN) TECHNOLOGY CO., LTD, Guangdong (CN); REHAB-ROBOTICS COMPANY LIMITED, Hong Kong (CN)

(72) Inventors: Mingjun Xia, Guangdong (CN); Wei Liang, Guangdong (CN); Guofu Fu, Guangdong (CN); Jialin Cai, Guangdong (CN); Peiyong Xu, Guangdong (CN); Yongjian Chen, Guangdong (CN)

(73) Assignees: VINCENT MEDICAL (DONG GUAN) MANUFACTURING CO., LTD, Guangdong (CN); VINCENT MEDICAL (DONG GUAN) TECHNOLOGY CO., LTD, Guangdong (CN); REHAB-ROBOTICS COMPANY LIMITED, Hong Kong (CN)

( * ) Notice: Subject to any disclaimer, the term of this patent is extended or adjusted under 35 U.S.C. 154(b) by 314 days.

(21) Appl. No.: 18/546,892

(22) PCT Filed: Mar. 23, 2023

(86) PCT No.: PCT/CN2023/083284
§ 371 (c)(1),
(2) Date: Aug. 17, 2023

(87) PCT Pub. No.: WO2023/179700
PCT Pub. Date: Sep. 28, 2023

(65) Prior Publication Data
US 2025/0009298 A1 Jan. 9, 2025

(30) Foreign Application Priority Data

Mar. 25, 2022 (CN) .......................... 202210300054.4

(51) Int. Cl.
*A61B 5/00* (2006.01)
*A61B 5/11* (2006.01)
*A61F 5/01* (2006.01)

(52) U.S. Cl.
CPC .......... *A61B 5/6812* (2013.01); *A61B 5/1121* (2013.01); *A61F 5/0123* (2013.01);
(Continued)

(58) Field of Classification Search
CPC ................ A61B 5/6812; A61B 5/1121; A61B 5/6811; A61B 5/1071; A61B 5/1126;
(Continued)

(56) References Cited

U.S. PATENT DOCUMENTS

| | | | | |
|---|---|---|---|---|
| 6,077,130 A * | 6/2000 | Hughes | .............. | H01R 13/2442 439/862 |
| 2010/0130893 A1 | 5/2010 | Sankai | | |
| 2024/0245381 A1* | 7/2024 | Morikawa | .............. | A61B 5/259 |

FOREIGN PATENT DOCUMENTS

| | | |
|---|---|---|
| CN | 107692964 A | 2/2018 |
| CN | 111772577 A | 10/2020 |

(Continued)

OTHER PUBLICATIONS

Machine Translation of Publication No. CN212395162U created Aug. 17, 2025 from Espacenet [retrieved from https://worldwide. espacenet.com/patent/search/family/074375413/publication/ CN212395162U?q=CN%20212395162] (Year: 2021).*

*Primary Examiner* — Alireza Nia
*Assistant Examiner* — Gina Mccarthy
(74) *Attorney, Agent, or Firm* — Muncy, Geissler, Olds & Lowe, P.C.

(57) ABSTRACT

The present disclosure provides a sensor and a knee joint brace. In the sensor and a knee joint brace, the sensor includes: a sensor bottom shell, a synchronous rotating component, an angle sensing instrument, and a circuit component arranged in sequence from bottom to top. One end of the synchronous rotating component is rotatably connected with the sensor bottom shell, and is used for connecting a support arm of the knee joint brace, and the other end of the (Continued)

synchronous rotating component is connected to the angle sensing instrument. The angle sensing instrument is electrically connected to the circuit component. The synchronous rotating component is arranged, and a movement state of a support arm of the knee joint brace is synchronized. The angle sensing instrument is arranged and is connected to the synchronous rotating component.

9 Claims, 7 Drawing Sheets

(52) U.S. Cl.
      CPC ..... *A61B 2505/09* (2013.01); *A61B 2562/166* (2013.01); *A61B 2562/18* (2013.01)
(58) Field of Classification Search
      CPC ................ A61B 5/6828; A61B 5/1116; A61B 5/1118; A61B 2505/09; A61B 2562/166; A61B 2562/18; A61B 5/107; A61H 1/024; A61H 3/00; A61H 2205/102
      See application file for complete search history.

(56)                    References Cited

FOREIGN PATENT DOCUMENTS

| CN | 212395162 | U | * | 1/2021 | ............ A61B 5/107 |
|----|-----------|---|---|--------|------------------------|
| CN | 114788694 | A |   | 7/2022 | |
| KR | 20180089126 | A | | 8/2018 | |
| WO | WO 2022027845 | A1 | | 2/2022 | |

* cited by examiner

21

22

SENSOR AND KNEE JOINT BRACE

TECHNICAL FIELD

The present disclosure relates to the technical field of rehabilitation protective gears, and in particular, to a sensor and a knee joint brace.

BACKGROUND

A knee joint is one of the joints with high load-bearing capacity and complex structure in a human body. Knee joint diseases often occur in daily life, leading to limitation of movement of the human body and seriously reducing the quality of life. In order to alleviate the damage of the knee joint diseases to the human body and improve the quality of life, a knee joint brace is provided in the related art. A support structure (such as a support arm) is arranged on the periphery of the knee joint to assist in supporting bones associated with the knee joint and to assist in fixing and supporting the knee joint, which can provide powerful protection and support for people with knee discomfort, relieve pain and discomfort in the knee joint, and provide walking support for part people with walking disabilities to a certain extent, thereby reducing the limitation of the movement of the human body and improving their quality of life to a certain extent.

However, for most patients with the knee joint diseases, they not only need to reduce the limitation of the movement simply, but also need to undergo rehabilitation exercises to achieve a purpose of recovering as soon as possible. Meanwhile, in order to better monitor and guide the rehabilitation exercises of the patients, it is often necessary to record rehabilitation exercise indicators and movement indexes such as a leg bending angle, a bending frequency, and a number of bending times of a user. However, the existing knee brace have these functions.

Therefore, the related art has defects and disadvantages, and needs to be further improved and developed.

SUMMARY

In view of the disadvantages in the related art, an objective of the present disclosure is to provide a sensor and a knee brace, which aims to solve the problems that a knee joint in the related art cannot sense and record rehabilitation exercise indicators and movement indexes of the knee joint of a user.

A technical solution used for solving technical problems in the present disclosure is as follows: a sensor, used for a knee joint brace, includes: a sensor bottom shell, a synchronous rotating component, an angle sensing instrument, and a circuit component arranged in sequence from bottom to top.

One end of the synchronous rotating component is rotatably connected with the sensor bottom shell, and is used for connecting a support arm of the knee joint brace, and the other end of the synchronous rotating component is connected to the angle sensing instrument.

The angle sensing instrument is electrically connected to the circuit component.

Further, the synchronous rotating component includes:

a rivet, one end of the rivet extending out from the sensor bottom shell, and being used for connecting a support arm of the knee joint brace; and a transmission shaft pick, one end of the transmission shaft pick being connected to the other end of the rivet, and the other end of the transmission shaft pick being connected to the angle sensing instrument.

Further, the rivet includes:

a rivet rod, a limiting surface being formed on the rivet rod, and the rivet rod being used for connecting the support arm of the knee joint brace; and a rivet cap, the rivet cap being arranged at one end, close to the transmission shaft pick, of the rivet rod, and a pick connecting slot being formed in the rivet cap.

Further, the transmission shaft pick includes:

a pick body;

a rivet connecting part, the rivet connecting part being arranged on an end face, facing the rivet cap, of the pick body; and a sensing instrument connecting part, the sensing instrument connecting part being arranged on an end face, facing the angle sensing instrument, of the pick body, and the sensing instrument connecting part being connected to the angle sensing instrument.

Further, the angle sensing instrument includes:

a sensing instrument body;

a rotary connecting part, the rotary connecting part being arranged on one side, facing the transmission shaft pick, of the sensing instrument body, and the rotary connecting part being clamped with the sensing instrument connecting part; and a connecting electrode, the connecting electrode being arranged on the sensing instrument body, and the connecting electrode being connected to the circuit component.

Further, the connecting slot is arranged as a D-shaped slot, a transverse 1-shaped slot, or a cross-shaped slot; the rivet connecting part is correspondingly arranged as a D-shaped convex rib, a transverse 1-shaped convex rib, or a cross-shaped convex rib;

the sensing instrument connecting part is arranged as a D-shaped convex rib, a transverse 1-shaped convex rib, or a cross-shaped convex rib; the rotary connecting part is correspondingly arranged as a D-shaped slot, a transverse 1-shaped slot, or a cross-shaped slot;

a first mark point is formed on the rivet connecting part; and a second mark point is formed on the sensor bottom shell.

Further, the circuit component includes:

a first PCB, the first PCB being arranged on the angle sensing instrument and being electrically connected with the angle sensing instrument;

a second PCB, the second PCB being arranged on the first PCB at an interval;

a storage battery, the storage battery being arranged between the first PCB and the second PCB and both being electrically connected to the first PCB and the second PCB;

a storage module, the storage module being arranged on the first PCB; and a data transmission module, the data transmission module being arranged on the first PCB.

Further, the sensor further includes:

a sensor shell, the sensor shell covering the sensor bottom shell, the synchronous rotating component, the angle sensing instrument, and the circuit component;

a function button, the function button being arranged on the second PCB, and being exposed from the sensor shell;

an indicator lamp, the indicator lamp being arranged on the second PCB;

an indicator lampshade, the indicator lampshade being arranged on the indicator lamp, and being exposed from the sensor shell; and a lampshade water-proof ring, the lampshade water-proof ring being arranged on the indicator lampshade in a sleeving manner.

Further, the sensor further includes:

a shell water-proof ring, the shell water-proof ring being arranged on one side, deviating from the sensor shell, of the sensor bottom shell.

Another technical solution used for solving technical problems in the present disclosure is as follows: a knee joint brace, which includes the sensor as described above.

The present disclosure provides a sensor and a knee joint brace. The sensor includes: a sensor bottom shell, a synchronous rotating component, an angle sensing instrument, and a circuit component arranged in sequence from bottom to top. One end of the synchronous rotating component is rotatably connected with the sensor bottom shell, and is used for connecting a support arm of the knee joint brace, and the other end of the synchronous rotating component is connected to the angle sensing instrument. The angle sensing instrument is electrically connected to the circuit component. The synchronous rotating component is arranged, and then the movement state of a support arm of the knee joint brace can be synchronized. The angle sensing instrument is arranged and is connected to the synchronous rotating component, and then a movement state of a user can be obtained by detecting the movement state of the synchronous rotating component. Meanwhile, the circuit component is arranged and the angle sensing instrument is controlled to electrically connect the circuit component, and then a real-time movement state of the user detected by the angle sensing instrument can be converted into an electric signal for storage and transmission, thereby accurately obtaining rehabilitation exercise indicators and movement indexes of the user.

Figure 1:
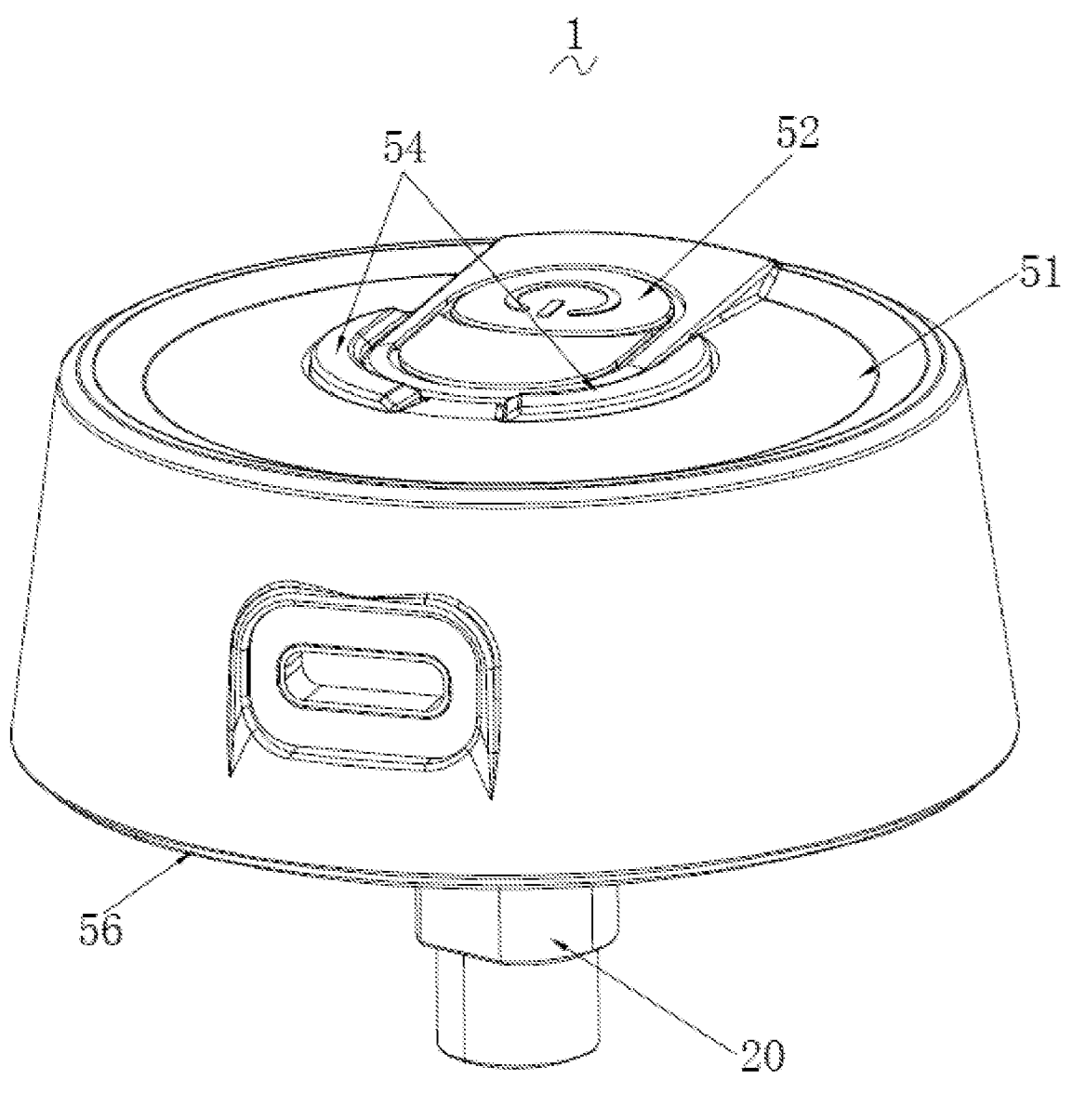
FIG. 1 is a schematic diagram of a three-dimensional structure of a sensor provided by the present disclosure.

Reference signs in the drawings:

1, sensor; 10, sensor bottom shell; 20, synchronous rotating component; 30, angle sensing instrument; 40, circuit component; 51, sensor shell; 52, function button; 53, indicator lamp; 54, indicator lampshade; 55, lampshade water-proof ring; 56, shell water-proof ring; 11, second mark point; 12, rotating hole; 21, rivet; 22, transmission shaft pick; 211, rivet rod; 212, limiting surface; 213, rivet cap; 214, pick connecting slot; 221, pick body; 222, rivet connecting part; 223, sensing instrument connecting part; 224, first mark point; 31, sensing instrument body; 32, rotary connecting part; 33, connecting electrode; 41, first Printed Circuit Board (PCB); 42, second PCB; 43, storage battery; 44, memory module; and 45 data transmission module.

DETAILED DESCRIPTION OF THE EMBODIMENTS

In order to make the purpose, technical solution, and advantages of the present disclosure more clear and definite, the present disclosure is further described in detail below with reference to the drawings and embodiments. It is to be understood that specific embodiments described herein are merely used for explain the present disclosure and are not intended to limit the present disclosure.

In the descriptions of the present disclosure, it is to be understood that orientations or positional relationships indicated by the terms "center", "longitudinal", "transverse", "upper", "lower", "front", "rear", "left", "right", "vertical", "horizontal", "top", "bottom", "inner", "outer", and the like are the orientations or positional relationships shown based on the drawings, and are merely for the convenience of describing the present disclosure and simplifying the description, rather than indicating or implying that the devices or elements must have particular orientations, and constructed and operated in particular orientations. Therefore, it cannot be construed as a limitation to the present disclosure. In addition, terms "first" and "second" are merely adopted for description and should not be understood to indicate or imply relative importance or implicitly indicate the number of indicated technical features. Therefore, a feature limited by "first" or "second" may explicitly or implicitly include one or more features. In the descriptions of the present disclosure, unless otherwise specified, "a plurality of" means at least two.

In the descriptions of the present disclosure, it is to be noted that, unless otherwise specified and defined explicitly, the terms "mounted", "interconnected", and "connected" are to be interpreted broadly, may be, for example, fixedly connected, or detachably connected, or integrally connected, may be mechanically connected, or electrically connected, may be directly connected, or indirectly connected through an intermediate, or internally communicated between two elements. Those of ordinary skill in the art can understand specific meanings of the above terms in the present disclosure based on specific situations.

A knee joint is one of the joints with high load-bearing capacity and complex structure in a human body. Knee joint diseases often occur in daily life, leading to limitation of movement of the human body and seriously reducing the quality of life. In order to alleviate the damage of the knee joint diseases to the human body and improve the quality of life, a knee joint brace is provided in the related art. A support structure is arranged on the periphery of the knee joint to assist in supporting bones associated with the knee joint and to assist in fixing and supporting the knee joint, which can provide powerful protection and support for people with knee discomfort, relieve pain and discomfort in the knee joint, and provide walking support for part people with walking disabilities to a certain extent, thereby reducing the limitation of the movement of the human body and improving their quality of life to a certain extent. However, for most patients with the knee joint diseases, they not only need to reduce the limitation of the movement simply, but also need to undergo rehabilitation exercises to achieve the purpose of recovering as soon as possible. Meanwhile, in order to better monitor and guide the rehabilitation exercises of the patients, it is often necessary to record rehabilitation exercise indicators and movement indexes such as a leg bending angle, a bending frequency, and a number of bending times of a user. However, the existing knee brace have these functions. Based on the problems that the knee joint brace in the related art cannot sensor and record rehabilitation exercise indicators and movement indexes of the knee joint of the user, the present disclosure provides a sensor and a knee joint brace. The synchronous rotating component is arranged, and then the movement state (that is, a movement state of the user) of a support arm of the knee joint brace can be synchronized. The angle sensing instrument is arranged and is connected to the synchronous rotating component, and then the movement state data (that is, rehabilitation exercise indicators and movement indexes, specifically, a leg bending angle, a bending frequency, a number of bending times of a user, and the like) of the user can be obtained by detecting the movement state of the synchronous rotating component. Meanwhile, the circuit component is arranged and the angle sensing instrument is controlled to electrically connect the circuit component, and then a real-time movement state of the user detected by the angle sensing instrument can be converted into an electric signal for storage and transmission, thereby accurately obtaining rehabilitation exercise indicators and movement indexes of the user. For details, please refer to the following embodiments.

Figure 5:
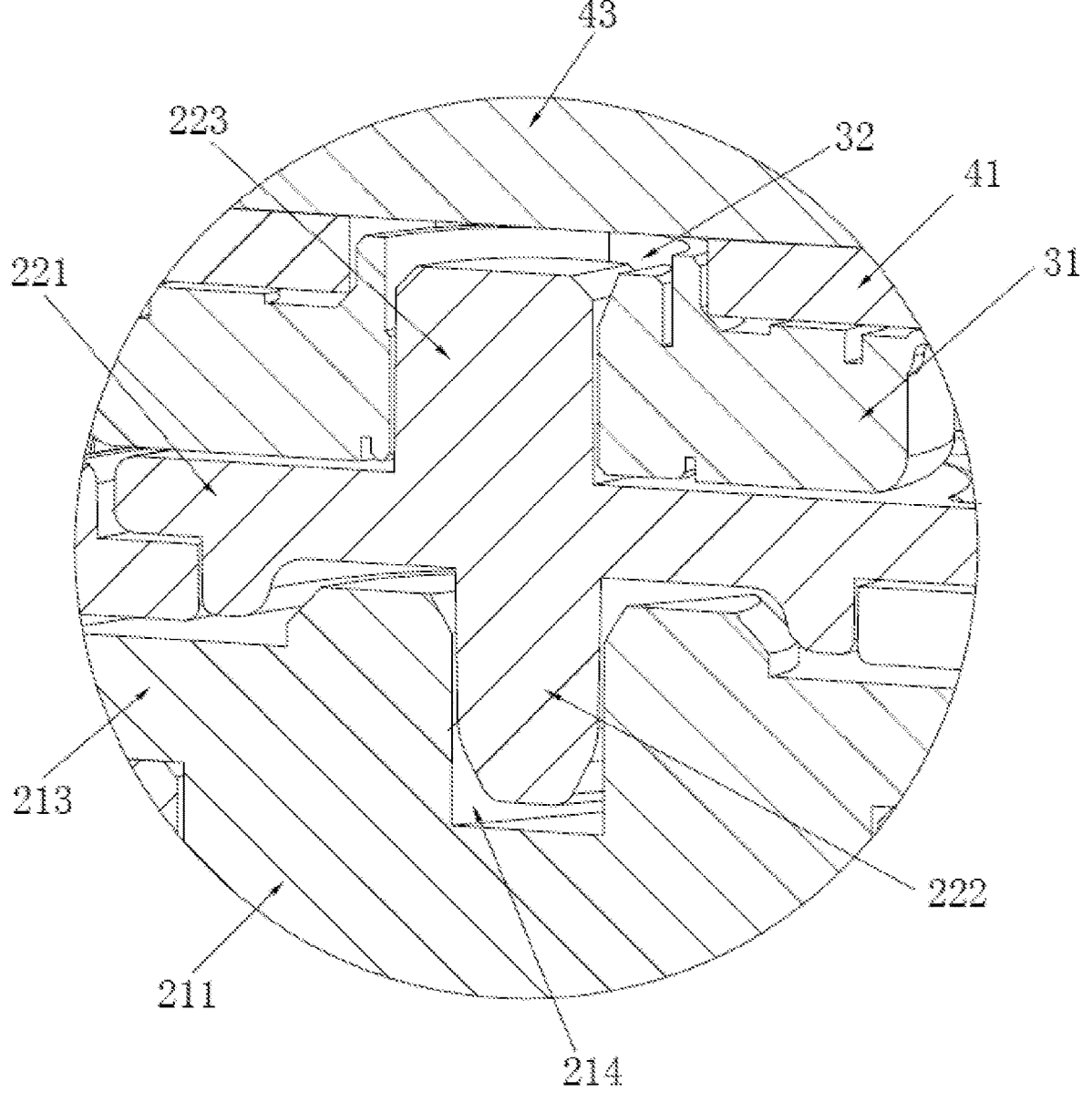
FIG. 5 is an enlarged schematic diagram of part A in FIG. 5 of the present disclosure.

Referring to FIG. 1 and FIG. 5, a first embodiment of the present disclosure provides a sensor 1, used for a knee joint brace, including a sensor bottom shell 10, a synchronous rotating component 20, an angle sensing instrument 30, and a circuit component 40 arranged in sequence from bottom to top. One end of the synchronous rotating component 20 is rotatably connected with the sensor bottom shell 10, and is used for connecting a support arm of the knee joint brace, and the other end of the synchronous rotating component 20 is connected to the angle sensing instrument 30. The angle sensing instrument 30 is electrically connected to the circuit component 40.

It is to be understood that the synchronous rotating component 20 can synchronize the movement state of the support arm of the knee joint brace. Since a support part of the knee joint brace is fixed to the leg at the knee joint of the user, then the synchronous rotating component 20 can synchronize the movement state of the leg of the user (such as a leg bending angle, a bending frequency, and a number of bending times of a user). Specifically, the synchronous rotating component 20 is arranged, and then the movement state (that is, the movement state of the user) of the support arm of the knee joint brace can be synchronized. The angle sensing instrument 30 is arranged and is connected to the synchronous rotating component 20, and then the movement state (such as the leg bending angle, the bending frequency, and the number of bending times) of the user can be obtained by detecting the movement state of the synchronous rotating component 20. Meanwhile, the circuit component 40 is arranged, the angle sensing instrument 30 is controlled to electrically connect the circuit component 40, and then a real-time movement state of the user detected by the angle sensing instrument 30 can be converted into an electric signal for storage and transmission, thereby accurately obtaining rehabilitation exercise indicators and movement indexes of the user.

In some implementations, the synchronous rotating component 20 includes: a rivet 21 and a transmission shaft pick 22. One end of the rivet 21 extends out from the sensor bottom shell 10, and is used for connecting a support arm of the knee joint brace. One end of the transmission shaft pick 22 is connected to the other end of the rivet 21, and the other end of the transmission shaft pick 22 is connected to the angle sensing instrument 30.

It is to be understood that when the knee joint brace is used and when the sensor 1 works, the synchronous rotating component 20 synchronously rotates with the support arm of the knee joint brace, that is, both the rivet 21 and the transmission shaft pick 22 will synchronously rotate. The rivet 21 is connected to the support arm of the knee joint brace. The transmission shaft pick 22 is connected to the rivet 21, and then the movement state of the support arm is synchronously transmitted to the angle sensing instrument 30, thereby providing guarantee for obtaining rehabilitation exercise indicators and movement indexes of the user.

Figure 6:
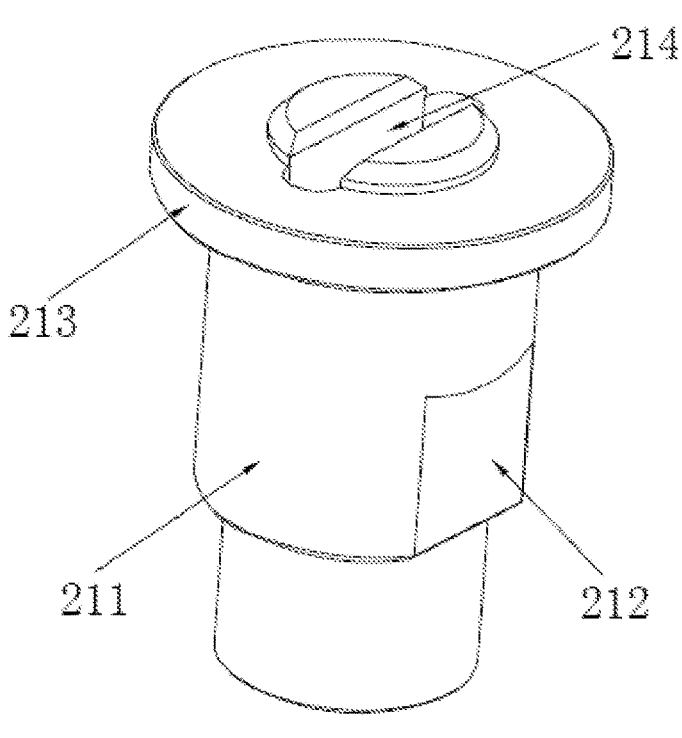
FIG. 6 is a schematic diagram of a three-dimensional structure of a rivet of the sensor provided by the present disclosure.

Further referring to FIG. 6, in some implementations, the rivet 21 includes: a rivet rod 211 and a rivet cap 213. A limiting surface 212 is formed on the rivet rod 211. The rivet rod 211 is used for connecting the support arm of the knee joint brace. The rivet cap 213 is arranged at one end, close to the transmission shaft pick 22, of the rivet rod 211, and a pick connecting slot 214 is formed in the rivet cap 213.

It is to be noted that a rotating hole 12 is formed in the sensor bottom shell 10. The hole diameter of the rotating hole 12 is adapted to the rivet rod 211. The hole diameter of the rotating hole 12 is smaller than the outside diameter of the rivet cap 213. The rivet rod 211 is rotatably connected to the sensor bottom shell 10. The limiting surface 212 is arranged, and then the connection stability between the rivet rod 211 and the support arm can be improved. The pick connecting slot 214 is formed, and then the connecting to the transmission shaft pick is facilitated.

Figure 7:
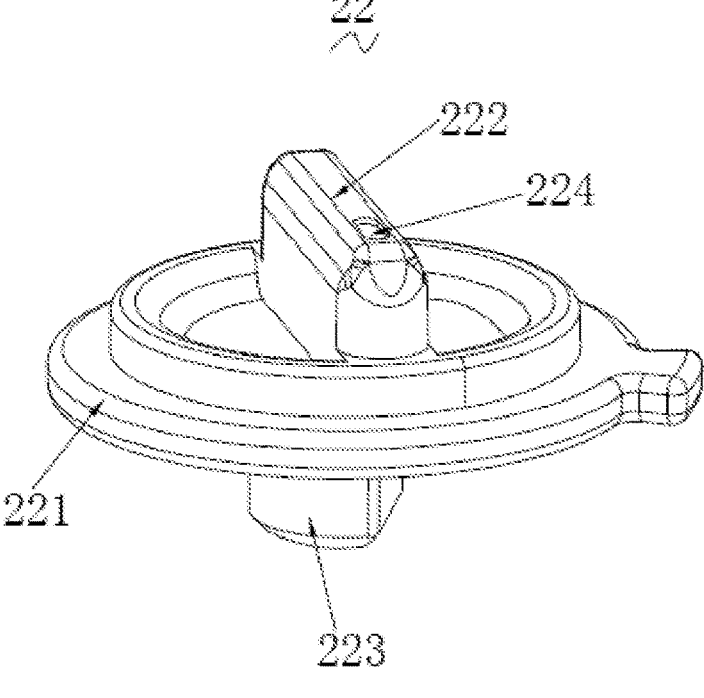
FIG. 7 is a schematic diagram of a three-dimensional structure of a transmission shaft pick of the sensor provided by the present disclosure.

Further referring to FIG. 7, in some implementations, the transmission shaft pick 22 includes: a pick body 221, a rivet connecting part 222, and a sensing instrument connecting part 223. The rivet connecting part 222 is arranged on an end face, facing the rivet cap 213, of the pick body 221. The rivet connecting part 222 is clamped with the connecting slot. The sensing instrument connecting part 223 is arranged on an end face, facing the angle sensing instrument 30, of the pick body 221, and the sensing instrument connecting part 223 is connected to the angle sensing instrument 30.

It is to be understood that the rivet connecting part 222 and the sensing instrument connecting part 223 are arranged on the pick body 221, then when the sensor 1 is assembled, the rivet connecting part 222 is conveniently clamped with the pick connecting slot 214 in the rivet cap 213, and meanwhile, the sensing instrument connecting part 223 is conveniently clamped with the angle sensing instrument 30, which facilitates the assembling of the sensor 1, and can also guarantee the connection stability among the rivet 21, the transmission shaft pick 22, and the angle sensing instrument 30.

Figure 8:
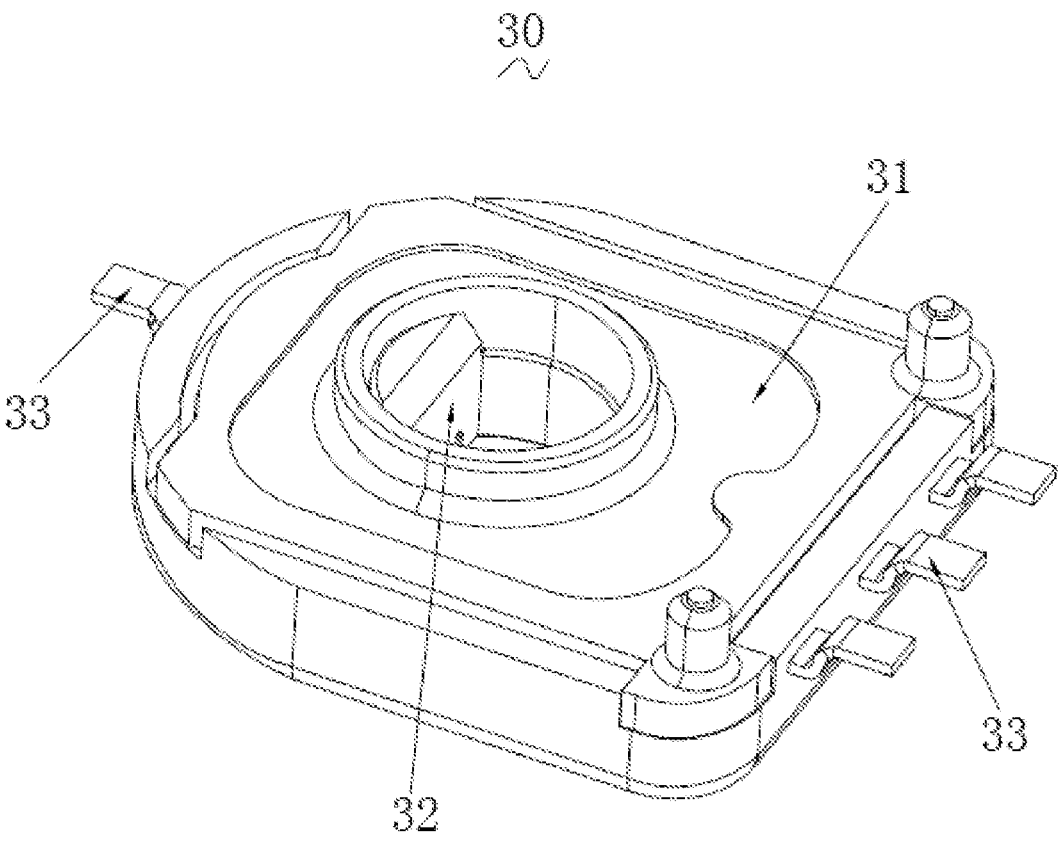
FIG. 8 is a schematic diagram of a three-dimensional structure of an angle sensing instrument of the sensor provided by the present disclosure.

Further referring to FIG. 8, in some other implementations, the angle sensing instrument 30 includes: a sensing instrument body 31, a rotary connecting part 32, and a connecting electrode 33. The rotary connecting part 32 is arranged on one side, facing the transmission shaft pick 22, of the sensing instrument body 31, and the rotary connecting part 32 is clamped with the sensing instrument connecting part 223. The connecting electrode 33 is arranged on the sensing instrument body 31, and the connecting electrode 33 is connected to the circuit component 40.

It is to be understood that the sensing instrument body 31 is connected to the sensing instrument connecting part 223 of the transmission shaft pick 22 through the rotary connecting part 32, and then accurate detection of the movement state of the synchronous rotating component 20 is guaranteed.

In some other implementations, the connecting slot is arranged as a D-shaped slot, and the rivet connecting part 222 is correspondingly arranged as a D-shaped convex rib; or the connecting slot is arranged as a transverse 1-shaped slot, and the rivet connecting part 222 is correspondingly arranged as a transverse 1-shaped convex rib; or the connecting slot is arranged as a cross-shaped slot, and the rivet connecting part 222 is correspondingly arranged as a cross-shaped convex rib.

It is to be understood that the shapes of the connecting slot and the rivet connecting part 222 are controlled, which not only facilitates the assembling of the sensor 1, but also guarantees the connection stability between the rivet 21 and the transmission shaft pick 22.

In some other implementations, the sensing instrument connecting part 223 is arranged as a D-shaped convex rib, and the rotary connecting part 32 is correspondingly arranged as a D-shaped slot; or the sensing instrument connecting part 223 is arranged as a transverse 1-shaped convex rib, and the rotary connecting part 32 is correspondingly arranged as a transverse 1-shaped slot; or the sensing instrument connecting part 223 is arranged as a cross-shaped convex rib, and the rotary connecting part 32 is correspondingly arranged as a cross-shaped slot.

It is to be understood that the shapes of the sensing instrument connecting part 223 and the rotary connecting part 32 are controlled, which not only facilitates the assembling of the sensor 1, but also guarantees the connection stability between the angle sensing instrument 30 and the transmission shaft pick 22.

Referring to FIG. 3 again, in some other implementations, a first mark point 224 is formed on the rivet connecting part 222; and a second mark point 11 is formed on the sensor bottom shell 10.

It is to be understood that the first mark point 224 is formed on the rivet connecting part 222 and the second mark point 11 is formed on the sensor bottom shell 10, and then initial angle installation and calibration of the sensor 1 are facilitated.

Figure 2:
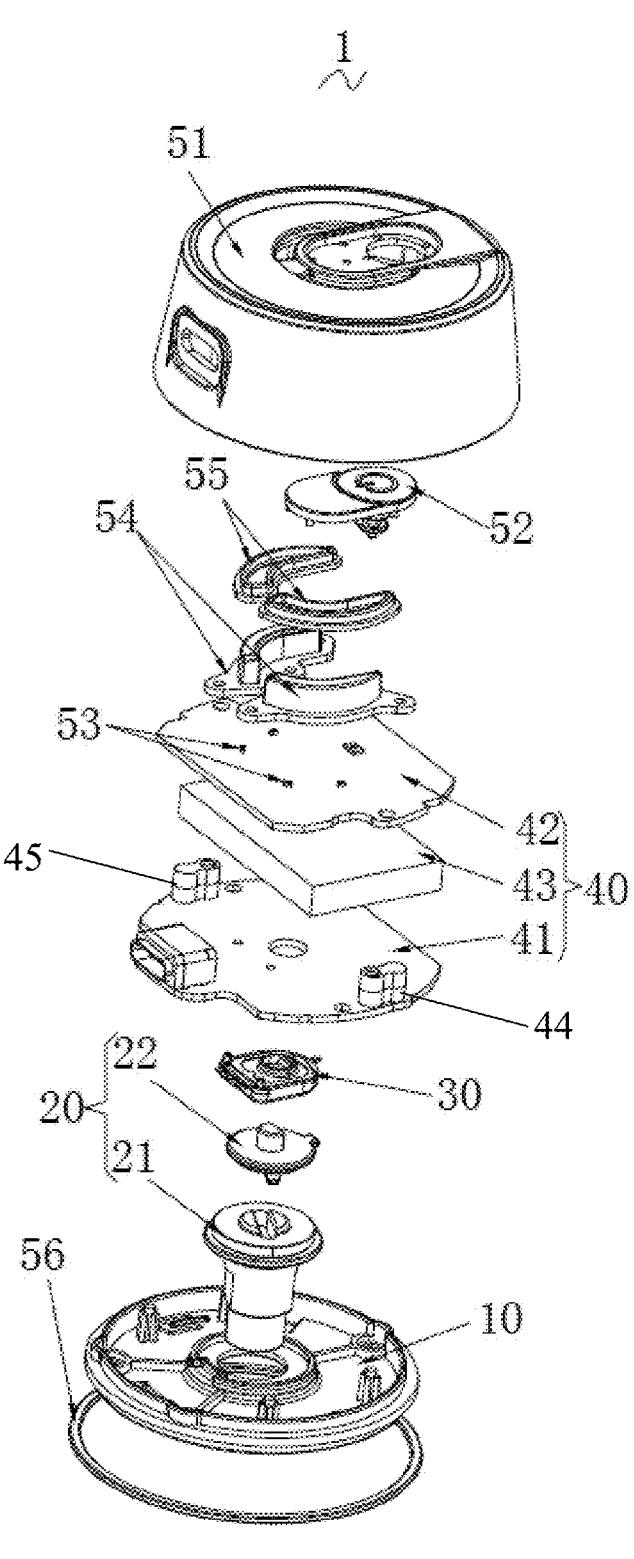
FIG. 2 is a three-dimensional exploded schematic diagram of the sensor provided by the present disclosure.
Figure 3:
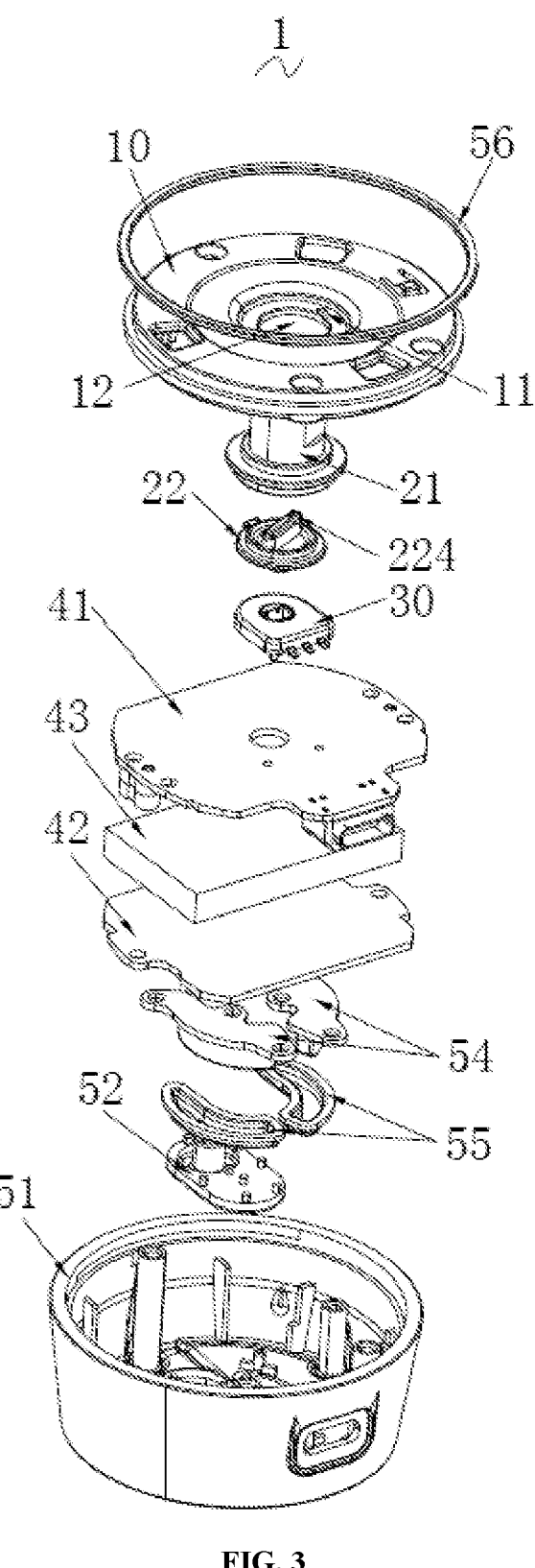
FIG. 3 is a three-dimensional exploded schematic diagram of the sensor in another perspective provided by the present disclosure.

Referring to FIG. 2 to FIG. 4 again, in some other implementations, the circuit component 40 includes a first PCB 41, a second PCB 42, a storage battery 43, a memory module 44, and a data transmission module 45. The first PCB 41 is arranged on the angle sensing instrument 30 and is electrically connected with the angle sensing instrument 30. The second PCB 42 is arranged on the first PCB 41 at an interval. The storage battery 43 is arranged between the first PCB 41 and the second PCB 42 and is electrically connected to both the first PCB 41 and the second PCB 42. The memory module 44 is arranged on the first PCB 41. The data transmission module 45 is arranged on the first PCB 41.

It is to be understood that the first PCB 41 and the second PCB 42 are simultaneously arranged, so that the overall appearance size of the sensor 1 can be reduced by only slightly increasing the thickness, thereby facilitating miniaturization of the sensor 1 and the knee joint brace. Meanwhile, the storage battery 43 is arranged, and the sensor 1 can monitor and record the movement state data of the user for a long time. The memory module 44 is arranged, and the converted movement parameters can be temporarily stored in time. The data transmission module 45 is arranged, and then the detected movement state data can be transmitted in time.

Referring to FIG. 2 to FIG. 4 again, in some other implementations, the sensor 1 further includes: a sensor shell 51, a function button 52, an indicator lamp 53, an indicator lampshade 54, and a lampshade water-proof ring 55. The sensor shell 51 covers the sensor bottom shell 10, the synchronous rotating component 20, the angle sensing instrument 30, and the circuit component 40. The function button 52 is arranged on the second PCB 42, and is exposed from the sensor shell 51. The indicator lamp 53 is arranged on the second PCB 42. The indicator lampshade 54 being arranged on the indicator lamp 53, and is exposed from the sensor shell 51. The lampshade water-proof ring 55 is arranged on the indicator lampshade 54 in a sleeving manner.

It is to be understood that the sensor shell 51 is arranged, and then the synchronous rotating component 20, the angle sensing instrument 30, and the circuit component 40 can be effectively protected. Meanwhile, the indicator lamp 53, the indicator lampshade 54, and the lampshade water-proof ring 55 are arranged and the indicator lamp 53 is controlled to expose from the sensor shell 51, and then the working state of the sensor 1 can be improved, and the sealing performance of the sensor 1 can also be guaranteed. The function button 52 is arranged, which facilitates controlling the operation of the sensor 1 by a user.

In some other implementations, the sensor 1 further includes: a shell water-proof ring 56. The shell water-proof ring 56 is arranged on one side, deviating from the sensor shell 51, of the sensor bottom shell 10, and then the sealing performance of the sensor 1 can be effectively improved.

Figure 4:
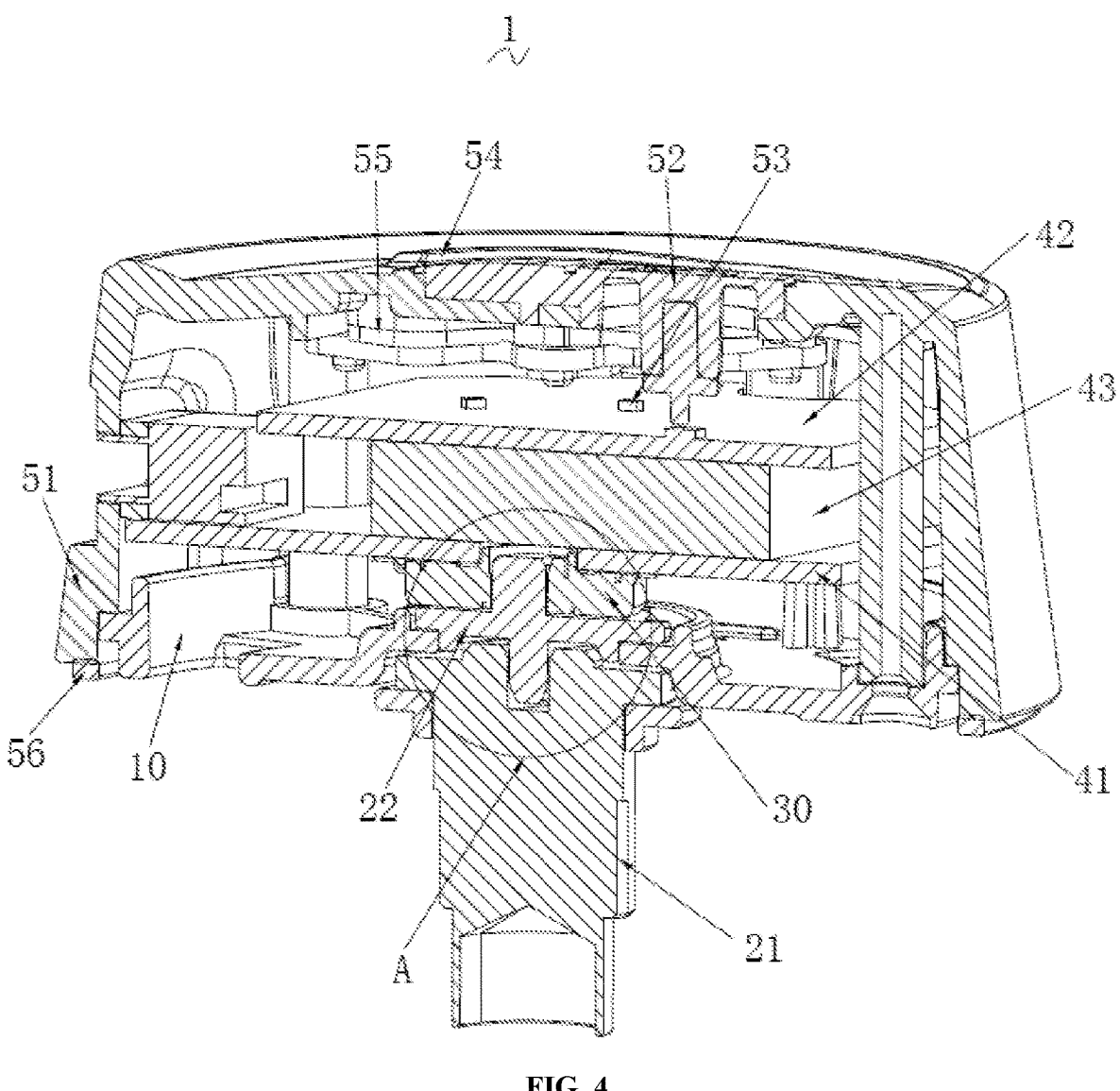
FIG. 4 is a sectional schematic diagram of the sensor provided by the present disclosure.

Referring to FIG. 4, a second embodiment of the present disclosure provides a knee joint brace, which includes the sensor 1 as described in the first embodiment of the present disclosure. It is to be understood that the knee joint brace provided in this embodiment adopts the sensor 1 provided in the first embodiment of the present disclosure, and then the movement state data of the user can be synchronously detected and obtained, thereby providing guarantee for obtaining rehabilitation exercise indicators and movement indexes of the user.

In conclusion, the present disclosure provides a sensor and a knee joint brace. The sensor includes: a sensor bottom shell, a synchronous rotating component, an angle sensing instrument, and a circuit component arranged in sequence from bottom to top. One end of the synchronous rotating component is rotatably connected with the sensor bottom shell, and is used for connecting a support arm of the knee joint brace, and the other end of the synchronous rotating component is connected to the angle sensing instrument. The angle sensing instrument is electrically connected to the circuit component. The synchronous rotating component is arranged, and then the movement state of a support arm of the knee joint brace can be synchronized. The angle sensing instrument is arranged and is connected to the synchronous rotating component, and then a movement state of a user can be obtained by detecting the movement state of the synchronous rotating component. Meanwhile, the circuit component is arranged and the angle sensing instrument is controlled to electrically connect the circuit component, and then a real-time movement state of the user detected by the angle sensing instrument can be converted into an electric signal for storage and transmission, thereby accurately obtaining rehabilitation exercise indicators and movement indexes of the user.

It is to be understood that the application of the present disclosure is not limited to the above examples. For those of ordinary skill in the art, improvements or transformations can be made according to the above description, and all these improvements and transformations shall fall within the protection scope of the claims attached to the present disclosure.

What is claimed is:

1. A sensor, used for a knee joint brace, comprising:
a sensor bottom shell;
a synchronous rotating component;
an angle sensing instrument; and
a circuit component arranged in sequence from bottom to top,
wherein one end of the synchronous rotating component is rotatably connected with the sensor bottom shell, and the other end of the synchronous rotating component is connected to the angle sensing instrument;
wherein the angle sensing instrument is electrically connected to the circuit component, and
wherein the synchronous rotating component comprises:
a rivet, one end of the rivet extending out from the sensor bottom shell, and another end of the rivet comprising a transmission shaft pick connecting slot extending along a first direction perpendicular to an axis direction of the rivet; and
a transmission shaft pick, one end of the transmission shaft pick comprising a rivet connecting part facing the rivet and extending along the first direction to be coupled with the transmission shaft pick connecting slot of the rivet, and another other end of the transmission shaft pick being connected to the angle sensing instrument.

2. The sensor according to claim 1, wherein the rivet comprises:
a rivet rod, a limiting surface being formed on the rivet rod, and the rivet rod extending out from the sensor bottom shell; and
a rivet cap, the rivet cap being arranged at one end, close to the transmission shaft pick, of the rivet rod, and the transmission shaft pick connecting slot being formed in the rivet cap.

3. The sensor according to claim 2, wherein the transmission shaft pick comprises:
a pick body;
the rivet connecting part, the rivet connecting part being arranged on an end face, facing the rivet cap, of the pick body; and
a sensing instrument connecting part, the sensing instrument connecting part being arranged on an end face, facing the angle sensing instrument, of the pick body, and the sensing instrument connecting part being connected to the angle sensing instrument.

4. The sensor according to claim 3, wherein the angle sensing instrument comprises:
a sensing instrument body;
a rotary connecting part, the rotary connecting part being arranged on one side, facing the transmission shaft pick, of the sensing instrument body, and the rotary connecting part being clamped with the sensing instrument connecting part; and
a connecting electrode, the connecting electrode being arranged on the sensing instrument body, and the connecting electrode being connected to the circuit component.

5. The sensor according to claim 4, wherein the circuit component comprises:
a first Printed Circuit Board (PCB), the first PCB being arranged on the angle sensing instrument and being electrically connected with the angle sensing instrument;
a second PCB, the second PCB being arranged on the first PCB at an interval;
a storage battery, the storage battery being arranged between the first PCB and the second PCB and being electrically connected to both the first PCB and the second PCB;
a memory module, the memory module being arranged on the first PCB; and
a data transmission module, the data transmission module being arranged on the first PCB.

6. The sensor according to claim 5, further comprising:
a sensor shell, the sensor shell covering the sensor bottom shell, the synchronous rotating component, the angle sensing instrument, and the circuit component;
a function button, the function button being arranged on the second PCB, and being exposed from the sensor shell;
an indicator lamp, the indicator lamp being arranged on the second PCB;
an indicator lampshade, the indicator lampshade being arranged on the indicator lamp, and being exposed from the sensor shell; and
a lampshade water-proof ring, the lampshade water-proof ring being arranged on the indicator lampshade in a sleeving manner.

7. The sensor according to claim 6, further comprising:
a shell water-proof ring, the shell water-proof ring being arranged on one side, deviating from the sensor shell, of the sensor bottom shell.

8. The sensor according to claim 4, wherein
the transmission shaft pick connecting slot is arranged as a D-shaped slot, a transverse 1-shaped slot, or a cross-shaped slot; the rivet connecting part is correspondingly arranged as a D-shaped convex rib, a transverse 1-shaped convex rib, or a cross-shaped convex rib;
the sensing instrument connecting part is arranged as a D-shaped convex rib, a transverse 1-shaped convex rib, or a cross-shaped convex rib; the rotary connecting part is correspondingly arranged as a D-shaped slot, a transverse 1-shaped slot, or a cross-shaped slot;
a first mark point is formed on the rivet connecting part; and a second mark point is formed on the sensor bottom shell.

9. A knee joint brace, comprising the sensor according to claim 1.

* * * * *